US009380270B1

(12) United States Patent
Worley, III et al.

(10) Patent No.: US 9,380,270 B1
(45) Date of Patent: Jun. 28, 2016

(54) SKIN DETECTION IN AN AUGMENTED REALITY ENVIRONMENT

(75) Inventors: William Spencer Worley, III, Half Moon Bay, CA (US); Ning Yao, Cupertino, CA (US); Edward Dietz Crump, Santa Cruz, CA (US); Sowmya Gopalan, Cupertino, CA (US)

(73) Assignee: Amazon Technologies, Inc., Seattle, WA (US)

( * ) Notice: Subject to any disclaimer, the term of this patent is extended or adjusted under 35 U.S.C. 154(b) by 261 days.

(21) Appl. No.: 13/222,452

(22) Filed: Aug. 31, 2011

(51) Int. Cl.
*H04N 9/47* (2006.01)
*H04N 7/18* (2006.01)
*A61B 1/04* (2006.01)

(52) U.S. Cl.
CPC . *H04N 7/18* (2013.01); *A61B 1/041* (2013.01)

(58) Field of Classification Search
USPC .......................................................... 348/77
See application file for complete search history.

(56) References Cited

U.S. PATENT DOCUMENTS

| | | | |
|---|---|---|---|
| 6,792,136 B1* | 9/2004 | Niesen | 382/118 |
| 7,418,392 B1 | 8/2008 | Mozer et al. | |
| 7,539,330 B2 | 5/2009 | Rowe | |
| 7,720,683 B1 | 5/2010 | Vermeulen et al. | |
| 7,774,204 B2 | 8/2010 | Mozer et al. | |
| 2003/0053664 A1* | 3/2003 | Pavlidis | G06K 9/2018 382/117 |
| 2003/0149504 A1* | 8/2003 | Iwaki et al. | 700/117 |
| 2006/0115176 A1* | 6/2006 | Kanamori | G06T 5/003 382/266 |
| 2007/0043252 A1* | 2/2007 | Reid | B01J 23/56 585/652 |
| 2007/0043527 A1* | 2/2007 | Quan et al. | 702/104 |
| 2009/0318815 A1* | 12/2009 | Barnes | A61B 5/0062 600/473 |
| 2011/0024632 A1 | 2/2011 | Vincent et al. | |
| 2011/0037843 A1* | 2/2011 | Mori et al. | 348/77 |
| 2012/0223885 A1 | 9/2012 | Perez | |

FOREIGN PATENT DOCUMENTS

WO    WO2011088053 A2    7/2011

OTHER PUBLICATIONS

Angelopoulou, "The Reflectance Spectrum of Human Skin", Department of Computer & Information ScienceTechnical Reports (CIS), University of Pennsylvania, Dec. 20, 1999, 15 pages.
Nunez, "A Physical Model of Human Skin and Its Application for Search and Rescue", Dissertation, Air Force Institute of Technology, Wright-Patterson Air Force Base, Ohio, Dec. 2009, 205 pages.
Nunez, et al., "Detection of Human Skin in Near Infrared Hyperspectral Imagery", Air Force Institute of Technology, IGARSS, Jul. 2008, 2 pages.
Nunez, et al., "Detection of Human Skin in Near Infrared Hyperspectral Imagery", Air Force Institute of Technology, Downloaded on May 31, 2009 from IEEE Xplore, 4 pages.
Pinhanez, "The Everywhere Displays Projector: A Device to Create Ubiquitous Graphical Interfaces", IBM Thomas Watson Research Center, Ubicomp 2001, 18 pages.

* cited by examiner

*Primary Examiner* — Chikaodili E Anyikire
(74) *Attorney, Agent, or Firm* — Lee & Hayes, PLLC

(57) ABSTRACT

An augmented reality environment allows interaction between virtual and real objects. Wavelength modulated light with a known spectral signature available within the augmented reality environment is used to generate spectral reflectance data for objects within the environment. This reflectance data is used to determine whether objects or portions thereof are skin.

20 Claims, 9 Drawing Sheets

| Time 302 | Image Frame 304 | Sub-Frame 306 | Spectral State 308 ||
|---|---|---|---|---|
| | | | Projector State 310 | Camera State 312 |
| 0 | 1 | 1 | Red | Red |
| 1 | 1 | 2 | Green | Green |
| 2 | 1 | 3 | Blue | Blue |
| 3 | 1 | 4 | Non-visible | Non-visible |
| 4 | 2 | 1 | Red | Red |
| 5 | 2 | 2 | Green | Green |
| 6 | 2 | 3 | Blue | Blue |
| 7 | 2 | 4 | Non-visible | Blue |
| 8 | 3 | 1 | Red | Red |
| 9 | 3 | 2 | Green | Green |

| SKIN REFLECTANCE REFERENCE DATASTORE 114 | | | | | |
|---|---|---|---|---|---|
| DESIGNATION 602 | ULTRAVIOLET RESPONSE 604 | BLUE RESPONSE 606 | GREEN RESPONSE 608 | RED RESPONSE 610 | INFRARED RESPONSE 612 |
| Skin - A | ⌢ | ⌢ | ⌢ | ⌢ | ⌢ |
| Skin - B | ⌢ | ⌢ | ⌢ | ⌢ | ⌢ |
| Skin - C | ⌢ | ⌢ | ⌢ | ⌢ | ⌢ |
| Skin - D | — | ⌢ | ⌢ | ⌢ | ⌢ |
| Skin - E | ⌢ | ⌢ | ⌢ | ⌢ | ⌢ |
| Skin - F | NA | ⌢ | ⌢ | ⌢ | NA |
| User Smith | ⌢ | ⌢ | ⌢ | ⌢ | ⌢ |
| User Jones | ⌢ | ⌢ | ⌢ | ⌢ | ⌢ |

FIG. 6

SKIN DETECTION IN AN AUGMENTED REALITY ENVIRONMENT

BACKGROUND

Augmented reality environments allow interaction among users and real-world objects and virtual or computer-generated objects and information. This merger between the real and virtual worlds paves the way for new interaction opportunities including gestural input.

BRIEF DESCRIPTION OF THE DRAWINGS

The detailed description is described with reference to the accompanying figures. In the figures, the left-most digit(s) of a reference number identifies the figure in which the reference number first appears. The use of the same reference numbers in different figures indicates similar or identical components or features.

FIG. 3 is an illustrative time sequence of image sub-frames and associated spectral states.

FIG. 6 illustrates a skin reflectance reference datatstore.

DETAILED DESCRIPTION

Figure 1:
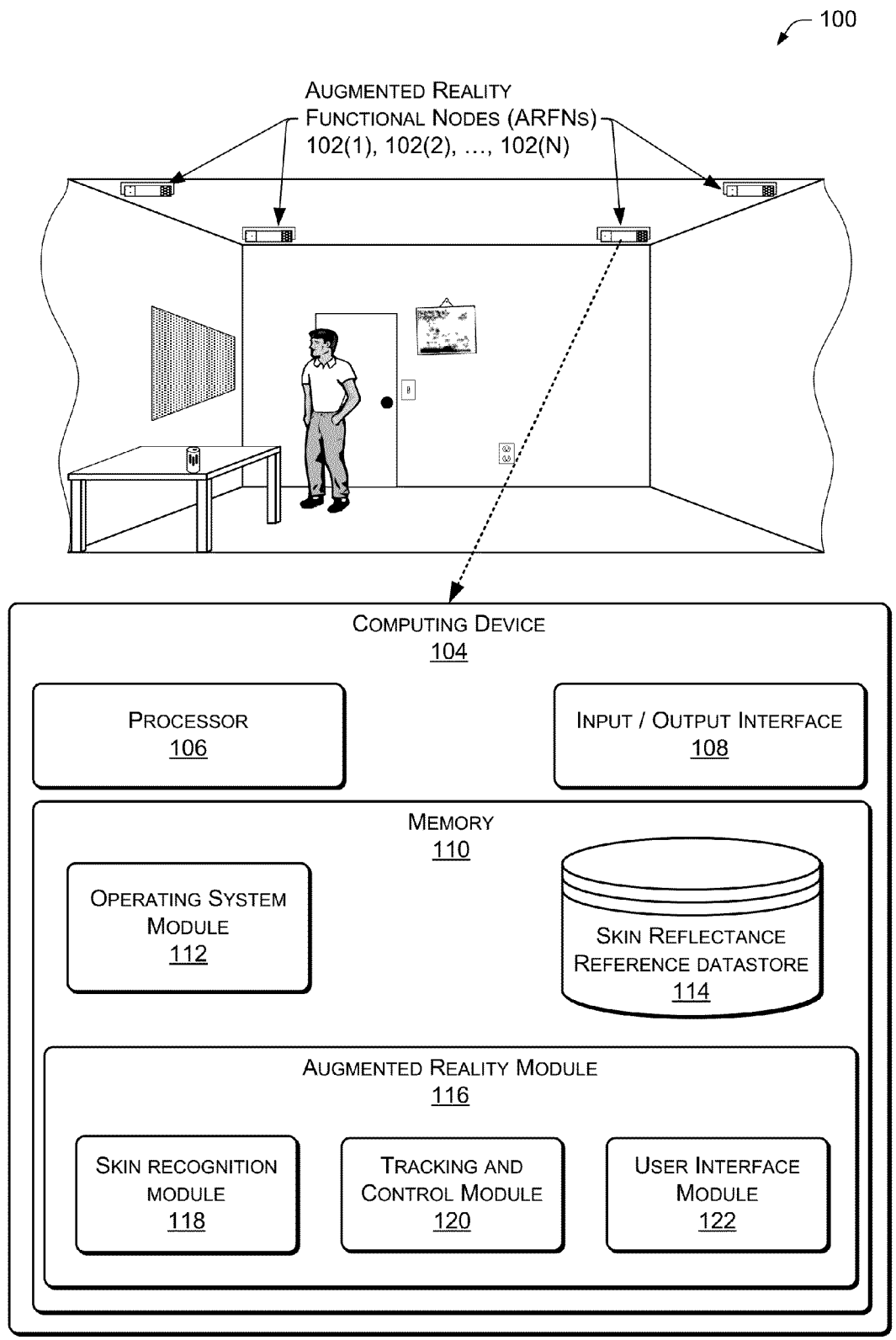
FIG. 1 shows an illustrative scene within an augmented reality environment which includes several augmented reality functional nodes and associated computing devices with skin recognition modules.

An augmented reality system may be configured to interact with objects within a scene and generate an augmented reality environment. The augmented reality environment allows for virtual objects and information to merge and interact with tangible real-world objects, and vice versa. Humans may use gestures, motions, positioning, orientation, or other attributes relating to body parts including, but not limited to, their hands, arms and face as input. For example, when accepting input such as hand gestures, it is worthwhile to know what part of the gesture is being made by a hand (skin) compared to what is from clothing, jewelry, and other (non-skin) objects.

Disclosed herein are techniques and devices suitable for using illumination with known characteristics in an augmented reality environment to determine whether an object, or portion thereof, is skin or not skin. Once this determination is made, other techniques may be applied to interpret the motion, orientation, or other attributes as input.

An augmented reality environment may be maintained using an augmented reality functional node (ARFN). The ARFN includes a projector and a camera. The projector and camera may be configured so their fields of projection and view, respectively, overlap at least in part. Thus, the projector may be configured to project an image onto an object which the camera may then see. The projector may be configured to generate wavelength modulated light, such that at particular times the scene and object(s) therein is illuminated with light having a known spectral signature. In some implementations the wavelength modulated light source may comprise an overhead light fixture, lamp, and so forth. The camera is configured to acquire spectral reflectance data resulting from reflectance of projector light from the object.

This spectral reflectance data includes spectral responses in one or more spectral bands or ranges of wavelengths. For example, the spectral reflectance data may include reflectance response curves for ultraviolet, blue, green, red, and infrared bands.

A skin reflectance reference datastore contains spectral reflectance data associated with objects having skin. "Skin" as used in this disclosure describes an exterior covering found on mammals, such as human skin. Skin may comprise several layers including the epidermis and dermis. Different layers and combinations of layers may exhibit different spectral reflectance at different wavelengths. The spectral reflectance data may be general or specific to a user. In some implementations, spectral reflectance data may be used at least in part to identify a particular user.

The spectral reflectance data is acquired while the object is illuminated by light with a known spectral signature. By comparing the spectral reflectance data with spectral reflectance data in the skin reflectance reference datastore, a skin recognition module determines when at least a portion of the object is skin. For example, a skin reflectance reference may have spectral reflectance data for human skin in the ultraviolet band showing absorption at about 335 nanometers (nm) corresponding to the absorptivity of the pigment melanin. While a shirtsleeve cuff may be reflective in the ultraviolet band, the melanin in the skin of the user's hand is more absorptive and thus less reflective. As a result, the portion of exposed skin may be determined to be skin due to its reflectance, and may therefore be differentiated from non-skin.

Illustrative Environment

FIG. 1 shows an illustrative augmented reality environment 100 which includes one or more augmented reality functional nodes (ARFNs) 102(1), 102(2), . . . , 102(N) with associated computing devices. In this illustration, multiple ARFNs 102(1)-(N) are positioned in the corners of the ceiling of the room. In other implementations, the ARFNs 102(1)-(N) may be positioned in other locations within the scene. When active, one such ARFN 102 may generate an augmented reality environment incorporating the scene. In some implementations, more or fewer ARFNs 102(1)-(N) may be used.

Each of the ARFNs 102(1)-(N) couples to or includes a computing device 104. This computing device 104 may be within the ARFN 102, or disposed at another location and connected to the ARFN 102. The computing device 104 comprises a processor 106, an input/output interface 108, and a memory 110. The processor 106 may comprise one or more processors configured to execute instructions. The instructions may be stored in memory 110, or in other memory accessible to the processor 106.

The input/output interface 108 may be configured to couple the computing device 104 to other components such as projector, cameras, microphones, other ARFNs 102, other computing devices, and so forth. The coupling between the computing device 104 and other components or devices may be via acoustic or electromagnetic communication methods. For example, the cameras may couple via Bluetooth to the computing device 104.

The memory 110 may include computer-readable storage media ("CRSM"). The CRSM may be any available physical media accessible by a computing device to implement the instructions stored thereon. CRSM may include, but is not limited to, random access memory ("RAM"), read-only memory ("ROM"), electrically erasable programmable read-only memory ("EEPROM"), flash memory or other memory technology, compact disk read-only memory ("CD-ROM"), digital versatile disks ("DVD") or other optical disk storage, magnetic cassettes, magnetic tape, magnetic disk storage or other magnetic storage devices, or any other medium which can be used to store the desired information and which can be accessed by a computing device.

Several modules such as instructions, datastores, and so forth may be stored within the memory 110 and configured to execute on a processor, such as the processor 106. Modules may be stored in the memory of the ARFN 102, storage devices accessible on the local network, or cloud storage accessible via a wide area network. An operating system module 112 is configured to manage hardware and services within and coupled to the computing device 104 for the benefit of other modules.

A skin reflectance reference datastore 114 is configured to maintain data about spectral response of skin to illumination with a known spectral signature. The skin reflectance reference datastore 114 may be stored on one or more of the memory of the ARFN 102, storage devices accessible on the local network, or cloud storage accessible via a wide area network. The skin reflectance reference datastore 114 is discussed in more detail below in regards to FIG. 6.

An augmented reality module 116 is configured to generate augmented reality output in concert with the physical environment. The module 116 may access the datastore 114 described herein. A skin recognition module 118 is configured to acquire and compare spectral reflectance data to determine if an object or at least a portion thereof is skin.

A tracking and control module 120 is configured to identify objects including users. This identification may include the use of a camera, structured light, spectral reflectance data, and so forth within the ARFN 102. The input may be determined to be from the user based at least in part upon the determination by the skin recognitions module 118 as to whether the object or a portion thereof is skin. A user interface module 122 is configured to accept and interpret input and generate output for the user. The ARFN 102 may use a camera, structured light, stereoscopic vision, and so forth to read the input from the user.

Figure 2:
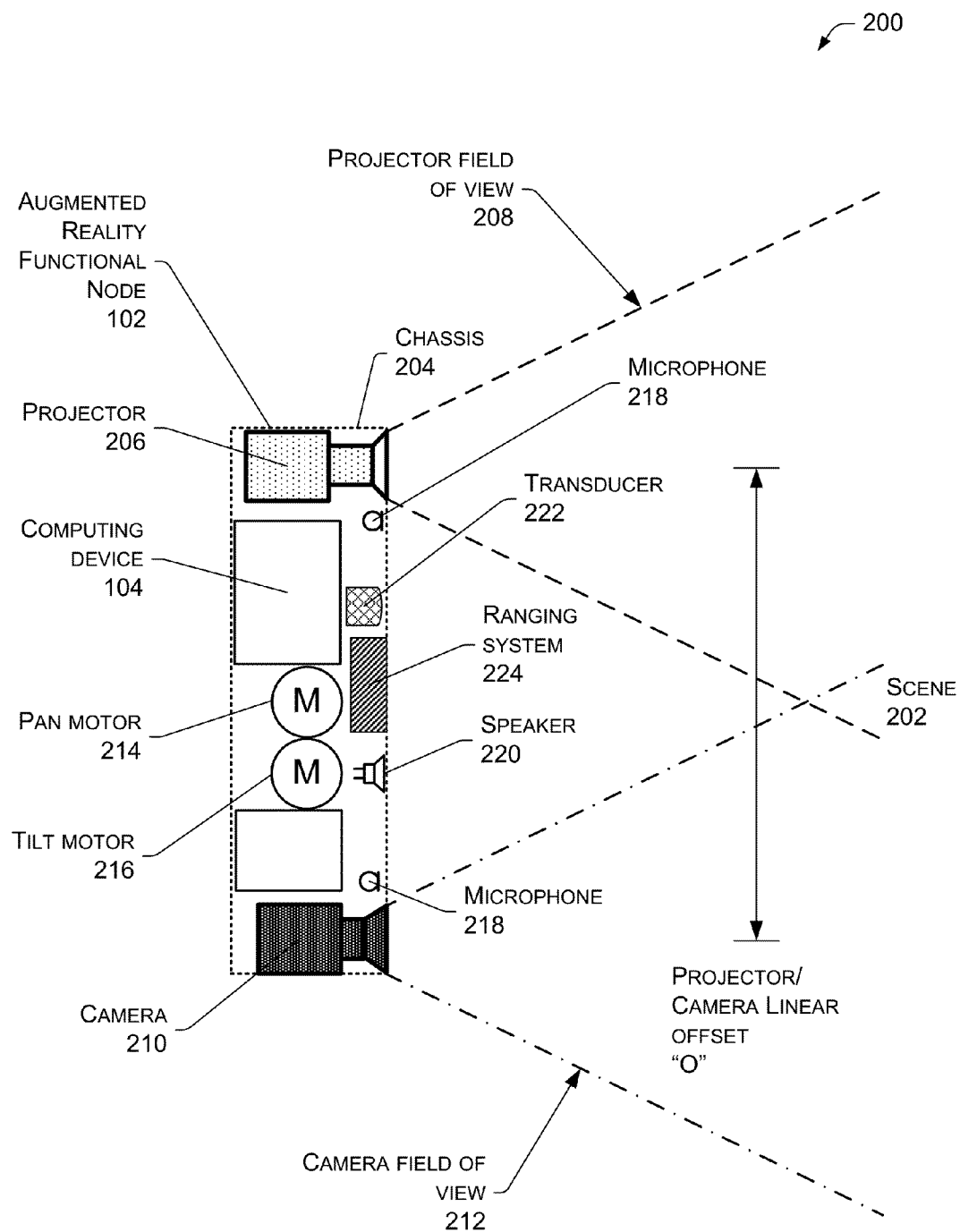
FIG. 2 shows an illustrative augmented reality functional node having a projector, a camera, and other selected components.

FIG. 2 shows an illustrative schematic 200 of one example augmented reality functional node 102 and selected components. The ARFN 102 is configured to scan at least a portion of a scene 202 and the objects therein. The ARFN 102 may also be configured to provide augmented reality output, such as images, sounds, and so forth.

A chassis 204 holds the components of the ARFN 102. Within the chassis 204 may be disposed a projector 206 that generates and projects images into the scene 202. These images may be visible light images perceptible to the user, visible light images imperceptible to the user, images with non-visible light, or a combination thereof. This projector 206 may be implemented with any number of technologies capable of generating an image and projecting that image onto a surface within the environment. Suitable technologies include a digital micromirror device (DMD), liquid crystal on silicon display (LCOS), liquid crystal display, 3LCD, and so forth. The projector 206 has a projector field of view 208 which describes a particular solid angle. The projector field of view 208 may vary according to changes in the configuration of the projector. For example, the projector field of view 208 may narrow upon application of an optical zoom to the projector. In some implementations, a plurality of projectors 206 or other displays such as televisions, monitors, and so forth may be used.

In some implementations the wavelength modulated light may be generated by one or more other sources, such as light fixtures. For example, the lights within a room such as a lamp, ceiling-mounted light, and so forth may comprise a plurality of light-emitting diodes and be configured to emit light in a particular spectral band at a particular time. In this implementation, the object may be illuminated to obtain reflectance data by the light fixture. This illumination may be instead of, or in addition to, illumination by the projector 206.

A camera 210 may also be disposed within the chassis 204. The camera 210 is configured to image the scene in visible light wavelengths, non-visible light wavelengths, or both. For example, in one implementation the camera 210 may be configured to generate a thermal image as well as a visible light image. The camera 210 has a camera field of view 212 which describes a particular solid angle. The camera field of view 212 may vary according to changes in the configuration of the camera 210. For example, an optical zoom of the camera may narrow the camera field of view 212. In some implementations, a plurality of cameras 210 may be used. The camera 210 may be configured to synchronize with the projector 206 or wavelength modulated light source such that images of the reflectance of light from a particular band are collected. This is described in more depth below with regards to FIG. 4.

The chassis 204 may be mounted with a fixed orientation, or be coupled via an actuator to a fixture such that the chassis 204 may move. Actuators may include piezoelectric actuators, motors, linear actuators, and other devices configured to displace or move the chassis 204 or components therein such as the projector 206 and/or the camera 210. For example, in one implementation the actuator may comprise a pan motor 214, tilt motor 216, and so forth. The pan motor 214 is configured to rotate the chassis 204 in a yawing motion. The tilt motor 216 is configured to change the pitch of the chassis 204. By panning and/or tilting the chassis 204, different views of the scene may be acquired. The spatial analysis module 114 may use the different views to monitor objects within the environment.

One or more microphones 218 may be disposed within the chassis 204, or elsewhere within the scene. These microphones 218 may be used to acquire input from the user, for echolocation, location determination of a sound, or to otherwise aid in the characterization of and receipt of input from the scene. For example, the user may make a particular noise, such as a tap on a wall or snap of the fingers, which are pre-designated as attention command inputs. The user may alternatively use voice commands. Such audio inputs may be located within the scene using time-of-arrival differences among the microphones and used to summon an active zone within the augmented reality environment.

One or more speakers 220 may also be present to provide for audible output. For example, the speakers 220 may be used to provide output from a text-to-speech module or to playback pre-recorded audio.

A transducer 222 may be present within the ARFN 102, or elsewhere within the environment, and configured to detect and/or generate inaudible signals, such as infrasound or ultrasound. For example, the transducer 222 may be configured to detect a characteristic ultrasonic sound signature produced by keys on a keyring. Inaudible signals may also be used to provide for signaling between accessory devices and the ARFN 102.

A ranging system 224 may also be provided in the ARFN 102. The ranging system 224 is configured to provide distance information from the ARFN 102 to a scanned object or set of objects. The ranging system 224 may comprise radar, light detection and ranging (LIDAR), ultrasonic ranging, stereoscopic ranging, and so forth. In some implementations the transducer 222, the microphones 218, the speaker 220, or a combination thereof may be configured to use echolocation or echo-ranging to determine distance and spatial characteristics.

In this illustration, the computing device 104 is shown within the chassis 204. However, in other implementations all or a portion of the computing device 104 may be disposed in another location and coupled to the ARFN 102. This coupling may occur via wire, fiber optic cable, wirelessly, or a combination thereof. Furthermore, additional resources external to the ARFN 102 may be accessed, such as resources in another ARFN 102 accessible via a local area network, cloud resources accessible via a wide area network connection, or a combination thereof.

Also shown in this illustration is a projector/camera linear offset designated "O". This is a linear distance between the projector 206 and the camera 210. Placement of the projector 206 and the camera 210 at distance "O" from one another aids in the recovery of structured light data from the scene. The known projector/camera linear offset "O" may also be used to calculate distances, dimensioning, and otherwise aid in the characterization of objects within the scene 202. In other implementations the relative angle and size of the projector field of view 208 and camera field of view 212 may vary. Also, the angle of the projector 206 and the camera 210 relative to the chassis 204 may vary.

In other implementations, the components of the ARFN 102 may be distributed in one or more locations within the environment 100. As mentioned above, microphones 218 and speakers 220 may be distributed throughout the scene. The projector 206 and the camera 210 may also be located in separate chassis 204. The ARFN 102 may also include discrete portable signaling devices used by users to issue command inputs. For example, these may be acoustic clickers (audible or ultrasonic), electronic signaling devices such as infrared emitters, radio transmitters, and so forth.

FIG. 3 is an illustrative time sequence 300 of a wavelength modulation pattern comprising image sub-frames and associated spectral states. The projector 206 is configured to provide illumination at a given instant in time having a spectral signature which is known or can be determined. At different times, the scene may be illuminated with different spectral bands or colors of light. Stated another way, the projector 206 is configured to provide wavelength modulated light. This allows the camera 210 to recover reflectance data from the object in one or more spectral bands as illuminated by the projector 206.

The variation of sub-frames within a particular frame and a pattern of spectral states for the projector 206 and camera 210 as time progresses are illustrated. The table includes a first field 302 for a time sequence, a second field 304 for an image frame number, a third field 306 for a sub-frame number, and a spectral state field 308 which includes a projector state field 310 and a camera state field 312. The camera state field 312 is the spectral band being imaged by the camera at that time.

The table associates the time sequences in field 302, the image frame number in field 304, and the sub-frame number in field 306 with the corresponding spectral states in field 308.

For example, at the time 302 of zero, the first image frame 304 is in the process of being projected. As part of the projection of that first image frame 304, the first sub-frame 306 is projected with the projector state 310 configured to output red visible light and the camera 210 is configured to acquire the red spectral reflectance data resulting from the illumination. Thus, during the time 302 of zero, the red portion of the first image frame 304 is being projected which illuminates the object with light in the red spectral band while spectral reflectance data is being acquired by the camera 210 in the red camera state 312. During successive times 302 of one and two, the green and blue sub-frames 306 are presented with corresponding projector states 310 and corresponding camera states 312 which acquire spectral reflectance data. At this point, a color image comprising the three principal color channels has been generated. At the time 302 of three, the fourth sub-frame 306 of the first image frame is being projected. This fourth sub-frame 306 is configured to project a non-visible image. Thus, as shown here, the projector state 310 during the fourth sub-frame 306 is set to non-visible and camera state 312 is set to non-visible. Using this non-visible light, a non-visible image may be formed and non-visible spectral reflectance data may be acquired. As described above, this non-visible image is non-visible to users. The non-visible image may be formed with ultraviolet, infrared, or other wavelengths of light outside of the visible range of the user.

In some implementations, the non-visible sub-frame 306 may be configured with a duration different from that of the visible light sub-frames. For example, each of the fourth sub-frames 306 for non-visible light may have a duration of about 4 milliseconds (ms) while the visible light sub-frames 306 may have durations of about 8 milliseconds. Furthermore, the duration of the visible light sub-frames 306 may vary as well. In some implementations a dark sub-frame may be inserted which includes no illumination to allow for gathering data on ambient illumination. Such data may be used to adjust measured spectral reflectance data to compensate for ambient illumination.

The timing and distribution of non-visible sub-frames 306 within the wavelength modulation pattern may be configured to reduce or eliminate flicker perceptible to the eye. For example, an overall image frame rate 304 may be 60 hertz while the sub-frames 306 are modulated at 240 hertz, or 1 frame for every 4 sub-frames 306.

In some implementations the wavelength modulation pattern 300 may be adjusted dynamically. Thus, one or more of the frequency, duration, or sequencing of the non-visible light sub-frames may be changed. For example, when a level of motion or displacement of objects within a physical scene exceeds a pre-determined threshold, additional non-visible light sub-frames may be injected to increase the scanning rate of the scene in the non-visible band.

In another implementation, display settings or environmental conditions may result in a dynamic adjustment to the wavelength modulation pattern. For example, when ambient light increases, the number of non-visible light sub-frames may be reduced to increase the overall brightness of the projected image.

The spectral state 308 may be configured in some instances to account for photoreactive effects exhibited by objects. As a result, the illumination may be provided in one spectral band while the reflectance data is acquired in a different spectral band. For example, suppose that during time seven when the projector state 310 is non-visible the scene is being illuminated with ultraviolet light. The camera state 312 may be configured to accept light in the blue spectral band such as may result from fluorescence of materials when excited by ultraviolet light. For example, detergents used for cleaning clothing may contain optical brightening agents which absorb ultraviolet light and fluoresce in the blue spectral band. Thus the projector state 310 may be configured for illumination in the ultraviolet spectral band while the camera state 312 is configured to acquire reflectance data in the blue spectral band. In this implementation, the acquired reflectance data may actually comprise reflectance of some illuminated light as well as emitted light resulting from the fluorescence. It is to be appreciated that while the discussion of FIG. 3 has included numerous example values, other implementations may employ other values.

Figure 4:
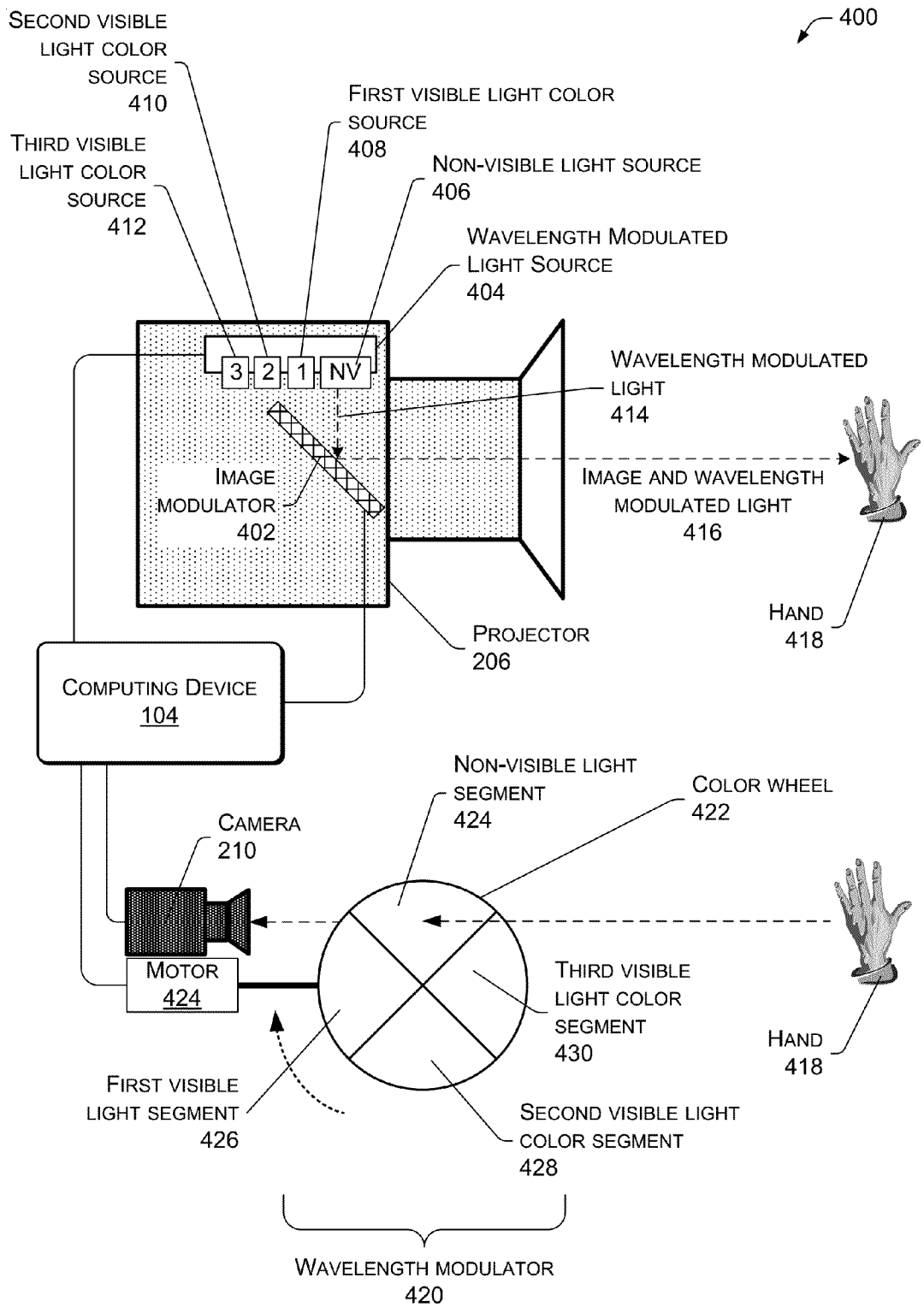
FIG. 4 is a schematic of the projector configured to illuminate an object and the camera configured to acquire light reflected by the object.

FIG. 4 is a schematic 400 of the projector 206 configured to illuminate an object and the camera 210 configured to acquire light projected by the projector 206 and reflected by the object. The projector 206 is illustrated with a wavelength modulated light source, configured to generate light with a known spectra signature within a given spectral band.

The projector 206 includes an image modulator 402 such as a digital micromirror device (DMD), liquid crystal, optical system to direct laser light, and so forth. The image modulator 402 spatially modulates light to produce an image. A wavelength modulator or wavelength modulated light source may be synchronized with the image modulator 402 such that when light having a particular spectral band or pre-determined range of wavelengths is being produced, a particular image may be generated therefrom.

A wavelength modulated light source 404 is depicted. As shown here, the wavelength modulated light source 404 comprises a plurality of emitters or sources of light varying wavelengths. A non-visible light source 406 is shown. Similarly, a first visible light color source 408, second visible light color source 410, and a third visible light color source 412 are also shown as part of the wavelength modulated light source 404. During operation, the wavelength modulated light source 404 generates wavelength modulated light 414 having a known or ascertainable spectral signature. By having both visible and non-visible light available, specific images may be rendered in particular wavelengths by the image modulator 402. As a result, objects within the scene such as a hand 418 may be illuminated with light in particular spectral bands at different times.

The light sources within the wavelength modulated light source 404 may comprise solid state devices such as lasers, light emitting diodes (LEDs), electro- or sono-luminescent materials, and so forth. These solid state light sources may be switched on and off allowing production of a particular pre-determined range of wavelengths, or a particular wavelength where the light source is monochromatic, at a particular time. In some implementations a multiple-wavelength light source with a color wheel may be used.

The wavelength modulated light source 404 is optically coupled to the image modulator 402 such that wavelength modulated light 414 may be used to generate a wavelength modulated light 416 image. The computing device 104 may coordinate the image modulator 402 and the wavelength modulated light source 404.

Also coupled to the computing device 104 is the camera 210, configured to acquire the spectral reflectance data from the object, such as the hand 418. The camera 210 may be coupled to a wavelength modulator 420. The wavelength modulator 420 is configured to selectively pass a pre-determined range of wavelengths for a given interval of time.

In the implementation shown in this figure, the wavelength modulator 420 comprises a color wheel 422 coupled to a motor 424. The color wheel 422 comprises a plurality of segments. Each segment of the color wheel is configured to pass a pre-determined range of wavelengths or spectral band. These wavelengths may be visible or non-visible. The motor 424 rotates the color wheel, as indicated by an arrow, such that for a given moment of time while a segment is in an optical path, the particular pre-determined range of wavelengths of that segment may pass. As the color wheel 422 rotates, over time the pre-determined range of wavelengths changes according to the sequence of the segments on the color wheel.

The color wheel 422 is illustrated with four segments, one for non-visible light and three for visible light. Four segments are shown by way of illustration, and not as a limitation. More or fewer segments may be used. Furthermore, in some implementations multiple segments may be configured to pass the same pre-determined range of wavelengths.

A non-visible light segment 424 is configured to pass a pre-determined range of non-visible wavelengths. These non-visible wavelengths are outside of the range of wavelengths visible to the user. For example, non-visible wavelengths may be longer or shorter than the range of wavelengths visible to the user. In one implementation, the non-visible wavelengths are in an ultraviolet portion of the spectrum. For ease of illustration and not by way of limitation one non-visible light segment 424 is shown here. In other implementations additional non-visible light segments 424 may be present on the color wheel 422.

Three visible light color segments are also shown in this illustration: a first visible light color segment 426, a second visible light color segment 428, and a third visible light color segment 430. For example, in some implementations these may correspond to red, green, and blue filters suitable for the reproduction of a color image from a generally white light source. It is understood that the number of colors and associated color gamut used may vary. For example, another implementation may use a red, green, blue, yellow gamut.

After being filtered by the wavelength modulator 420, the un-modulated light from the object such as the hand 418 becomes wavelength modulated light. This filtering may in some implementations reduce noise from ambient illumination. The wavelength modulated light may then be imaged by an imaging element of the camera 210.

In another implementation the wavelength modulator 420 may be omitted, such as in instances when the lighting in the room containing the augmented reality environment is controlled or synchronized with the illumination and acquisition. In this case, the objects in the scene are illuminated primarily or exclusively by the pre-determined illumination.

In another implementation the camera 210 may comprise a plurality of cameras. These cameras may share at least a portion of a common optical path. The cameras may be configured to each image in a particular band. For example, one camera may be configured to image in the red spectral band, another in blue, and a third in green. The output for the cameras may be synchronized with the projector 206 output.

Figure 5:
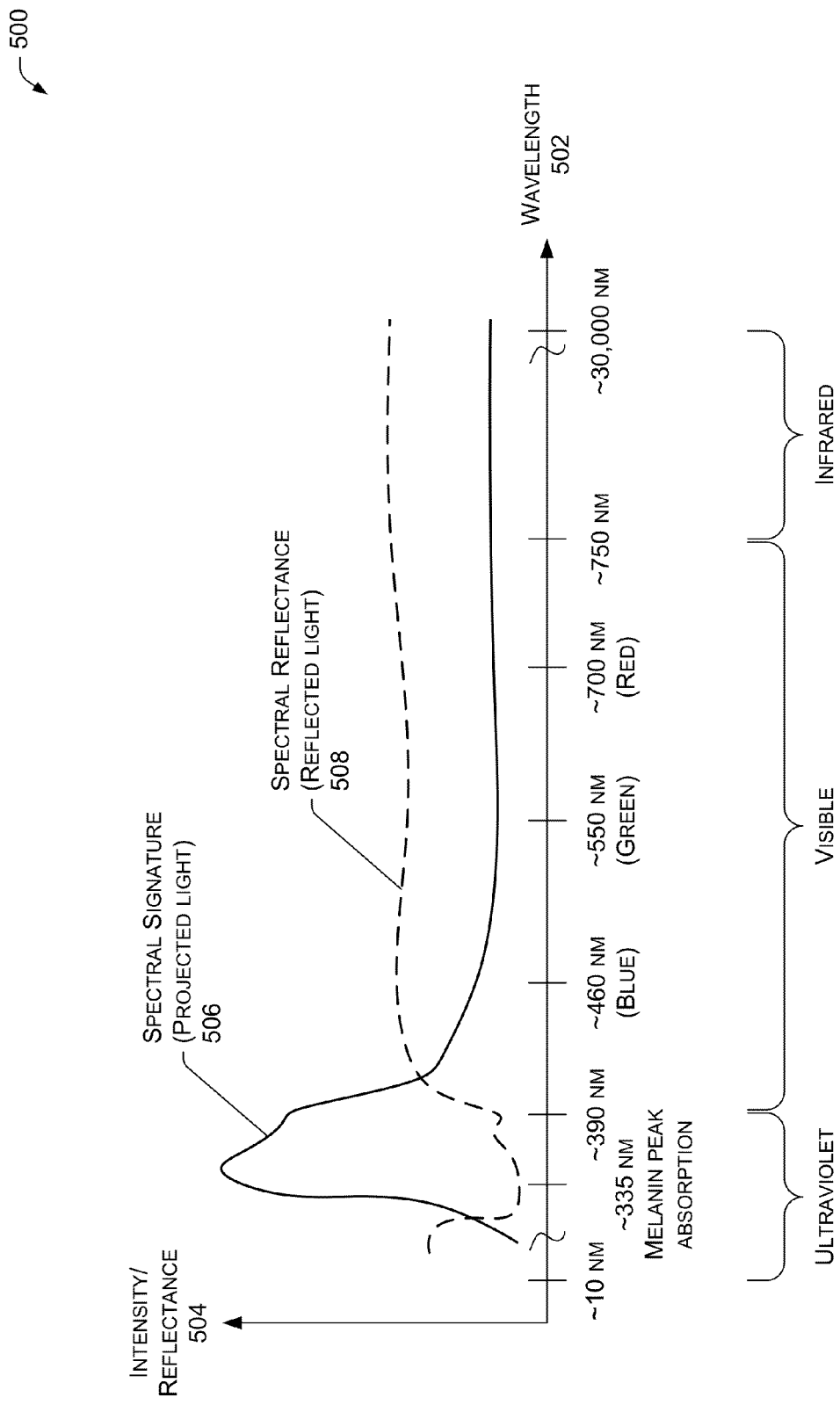
FIG. 5 is a graph illustrating, as a function of wavelength, the intensity of projected light and associated reflectance from an object.

FIG. 5 is a graph 500 illustrating a spectral signature of projected light illuminating an object and associated spectral reflectance from the object as a function of wavelength. In this chart the horizontal axis indicates a wavelength 502 while the vertical axis indicates an intensity of the illumination or reflectance 504 by the object. The distribution of points along the axes is not necessarily to scale.

Among the wavelengths shown and their designations on this chart is ultraviolet (UV) spectral band with a wavelength of about 10 nm to 390 nm. An absorption peak for the pigment melanin is shown within the ultraviolet band at about 335 nm. Melanin is a pigment typically found in human skin.

Visible light as shown extends from about 390 nm to 750 nm. Infrared (IR) is shown from about 750 nm to about 30,000 nm. The definition of visible and non-visible light may vary between users. For example, the typical human eye is considered capable of detecting the visible light wavelengths, but is generally incapable of detecting wavelengths outside of this range. Thus, UV and IR light are considered non-visible to the human eye.

The wavelength modulated light 414 generated by the projector or received by the imager within the camera 210 such as through the wavelength modulator 420 may be monochromatic. However, many actual light sources show some variation with wavelength. Shown here is a spectral signature 506 of projected light, such as in the non-visible UV band. This particular light source shows a peak at about 340 nm, then little or no output in the infrared. For example, a UV LED may exhibit such a spectral signature.

Also shown in this graph 500 is a spectral reflectance 508 resulting from the light from the projector reflecting from the object within the scene, such as the hand 418. Due to the absorption of the UV light by the melanin in the skin of the user's hand, the spectral reflectance 508 in the UV band is low. When a comparison determines the resulting spectral reflectance 508 matches previously stored spectral reflectance data designated as skin, the object may be determined to be skin. The spectral reflectance 508 as acquired at different times may also be stored, such as in the skin reflectance reference datastore 114. Such information allows for tracking of and adjustment due to changes in skin reflectance over time.

Skin reflectance as stored over time may be used to provide context cues to the augmented reality environment. For example, spectral reflectance 508 acquired from a population of users may indicate the skin reflectance changes for users as a function of the user's age. As a result, the spectral reflectance 508 may be used to estimate the age of a user.

FIG. 6 illustrates data 600 within the skin reflectance reference datatstore 114. The datastore 114 contains spectral reflectance data associated with objects having skin. The spectral reflectance data may be general such as derived from a population of samples, or specific to a user. In some implementations, spectral reflectance data may be used at least in part to identify a particular user.

The skin reflectance reference datastore 114 may comprise a designation 602, ultraviolet response 604, blue response 606, green response 608, red response 610, infrared response 612, and so forth. For example, as shown here skin designated "Skin—A" may be specified as having the spectral reflectance curves or response as shown across UV, blue, green, red, and IR bands. An object having spectral reflectance which matches within a pre-determined threshold range the curves in these bands would thus be determined to be "Skin—A".

In some implementations some designations may use only selected spectral bands. For example, as shown here "Skin—F" is shown as having visible light response curves but no ultraviolet or infrared response curves. As a result, an object which when illuminated by visible light in the blue, green, and red spectral bands has spectral reflectance which matches within a pre-determined threshold range would thus be determined to be "Skin—F".

Particular users may be identified in the augmented reality environment 100 based at least in part on the spectral reflectance of their skin. For example, "User Smith" and "User Jones" exhibit differing spectral reflectance curves in the UV, blue, green, and IR bands as shown in this illustration. These spectral reflectance curves may be associated with the particular user, such as "User Smith" or "User Jones" as shown here. Acquired spectral reflectance data may be compared with previously stored reflectance to attempt to identify the user. Thus, differences may be used to "fingerprint" and act as unique characteristics to aid in identification of the user when compared against previously stored reflectance data. In some implementations, the particular spectral reflectance of their skin may also be used in conjunction with other mechanisms such as voice recognition, facial recognition, and so forth.

Because spectral reflectance of skin may vary over time, in some implementations the augmented reality environment may maintain a history of spectral reflectance data for the user. In some implementations, the spectral reflectance data for the user may be stored and may also be adjusted over time to account for these changes. For example, consider a user who starts to spend time each day in a tanning booth. Over time, the user exhibits an increasingly darker skin tone due to increased ultraviolet exposure. During usage, the augmented reality environment may update the spectral reflectance data for this user to account for this gradual change. Or a user may experience sunburn after a day at the beach which results in an altered spectral reflectance. The augmented reality environment may update the spectral reflectance data for this user to account for this relatively sudden change as well.

Illustrative Processes

The processes described in this disclosure may be implemented by the architectures described herein, or by other architectures. These processes are illustrated as a collection of blocks in a logical flow graph. Some of the blocks represent operations that can be implemented in hardware, software, or a combination thereof. In the context of software, the blocks represent computer-executable instructions stored on one or more computer-readable storage media that, when executed by one or more processors, perform the recited operations. Generally, computer-executable instructions include routines, programs, objects, components, data structures, and the like that perform particular functions or implement particular abstract data types. The order in which the operations are described is not intended to be construed as a limitation, and any number of the described blocks can be combined in any order or in parallel to implement the processes. It is understood that the following processes may be implemented on other architectures as well.

Figure 7:
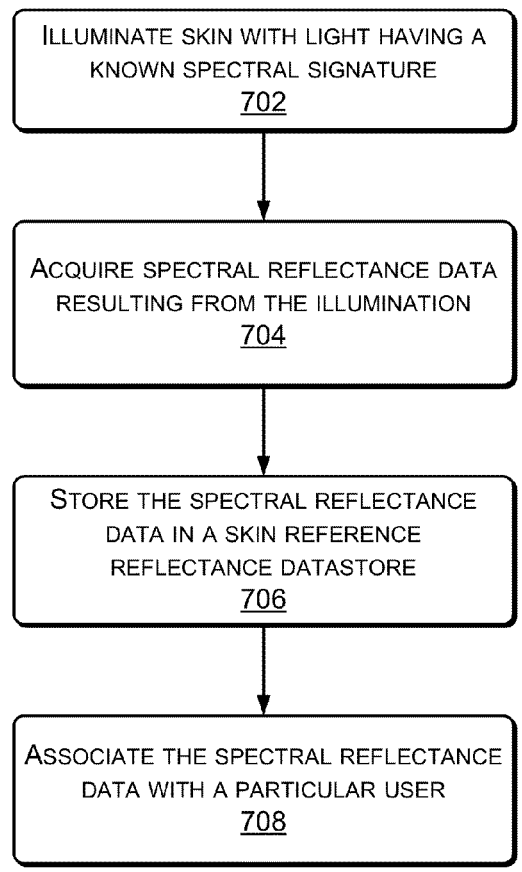
FIG. 7 is an illustrative process of populating the skin reflectance reference datastore with spectral reflectance data.

FIG. 7 is an illustrative process 700 of populating the skin reflectance reference datastore with spectral reflectance data. By providing a plurality of spectral reflectances for different skin types in different spectral bands, the system is better able to recognize skin even with variations in coloring, surface coatings such as cosmetics, sunscreens, and so forth.

At 702, skin is illuminated with light having a known spectral signature. The spectral signature may become known or calibrated by illuminating an object having pre-determined reflectance characteristics. As described above with regards to FIG. 3, this illumination may include visible light, non-visible light, or a combination thereof. The illumination may be provided by the projector 206, wavelength modulated room lights, and so forth.

At 704, spectral reflectance data resulting from the illumination is acquired. For example, the camera 210 may acquire an image in the spectral band corresponding to the illumination at about the same time as the illumination takes place.

At 706, the spectral reflectance data is stored in the skin reference reflectance datastore 114. As described above with regards to FIG. 6, this may include spectral reflectance data for one or more spectral bands.

In some implementations the spectral reflectance data may be associated with a particular user. For example, in some implementations other identification techniques such as password, fingerprint, facial recognition, voice recognition, biometrics, and so forth may be used to determine which user to associate the spectral reflectance data with. At 708, the spectral reflectance data is associated with the particular user.

Figure 8:
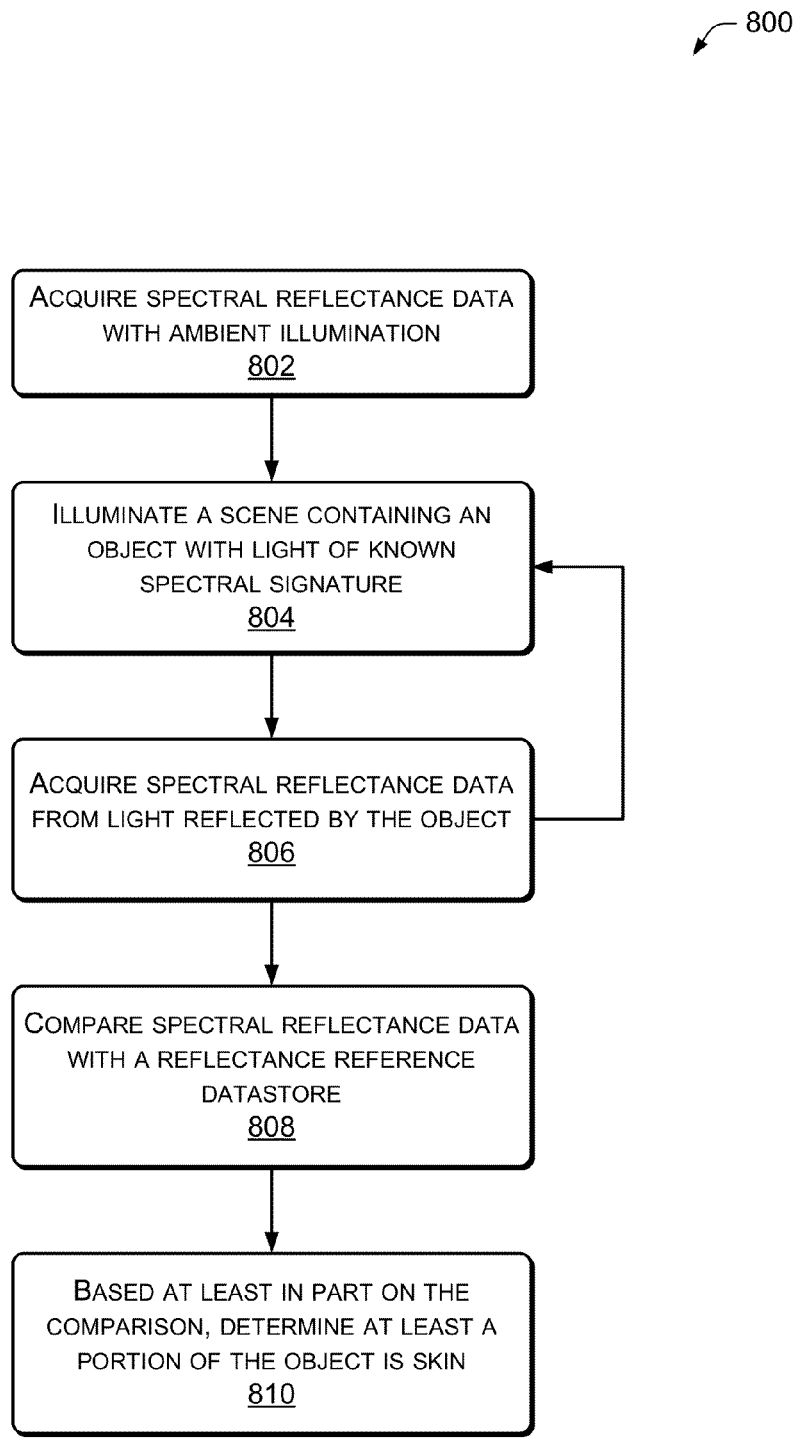
FIG. 8 is an illustrative process of sequentially illuminating an object with multiple known spectral bands and acquiring images to generate reflectance data and determining, based at least in part upon the reflectance data, that the object is skin.

FIG. 8 is an illustrative process 800 of illuminating an object with multiple known spectra and acquiring images to generate reflectance data and determining, based at least in part upon the reflectance data, that the object is skin. At 802, spectral reflectance data is acquired with ambient illumination. This spectral reflectance data may be used to calibrate subsequent spectral reflectance data to account for effects of the ambient illumination.

At 804, the scene containing the object is illuminated with light of a known spectral signature. For example, the projector 206 may be configured to illuminate the scene during a sub-frame with light in the green spectral band. Or an overhead wavelength modulated light fixture may be configured to illuminate the room briefly with light in the green spectral band.

The spectral signature may be known prior to illumination, such as where the light source of the projector 206 has been calibrated. In other implementations the spectral signature of the illumination may be determined at the time of illumination based upon reflectance from a calibration object having known reflectance characteristics.

At 806, spectral reflectance data from light reflected by the object is acquired. For example, one or more imaging devices such as the camera 210 acquires an image of the object. In some implementations, the scene may be illuminated sequentially with a plurality of different spectral bands. For example, data may be acquired from illumination in the red, green, and blue spectral bands.

At 808, the spectral reflectance data is compared with previously stored spectral reflectance data stored in the skin reflectance reference datastore 114. The skin reflectance reference datastore 114 may itself comprise a portion of a datastore containing reflectance reference data for other objects. The comparison may be configured to use one or more spectral bands, and apply a pre-determined threshold range to reflectance data (such as a reflectance curve) in these bands. The pre-determined threshold range may differ between spectral bands, designation 602, or both. For example, the threshold for a match for "Skin—A" may be ±5% in the blue spectral band and ±13% in the red spectral band.

At 810, based at least in part on the comparison, at least a portion of the object is determined to be skin. For example, based on the absorption of the ultraviolet light a portion of the object may be determined to be skin on a hand while another portion which is highly reflective or emissive may be determined to be a tabletop.

Figure 9:
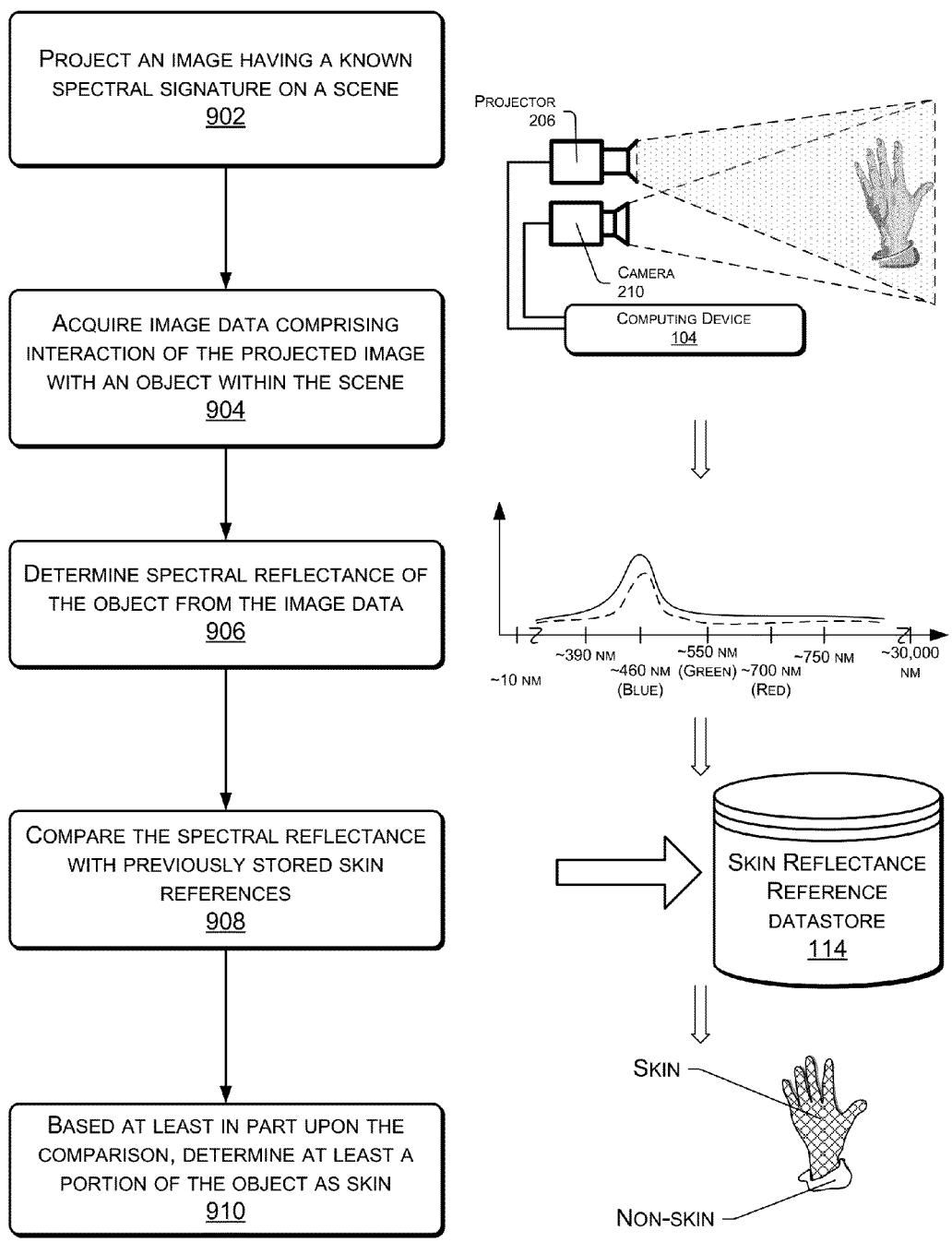
FIG. 9 is an illustrative process of determining whether or not at least a portion of an object is skin based at least in part on spectral reflectance.

FIG. 9 is an illustrative process 900 of determining whether or not at least a portion of an object is skin based at least in part on spectral reflectance. At 902, an image having a known spectral signature is projected onto a scene. This image serves to illuminate objects within the scene. This image may be generated by a wavelength modulated light source, such as the projector 206 as shown here. The image may comprise structured light which may incorporate regular patterns, pseudorandom patterns, or random patterns.

At 904, image data comprising interaction of at least a portion of the projected image with at least a portion of the object within the scene is acquired. For example the camera 210 may generate an image of the object as illuminated by the image. The camera 210 may be synchronized with the projector 206 or other wavelength modulated light source such that both are operating in the same spectral band at about the same time.

At 906, spectral reflectance of the object is determined from the image data. In some implementations this may include applying corrections or calibration factors to account for ambient light, changes in the spectral signature of the light source, and so forth.

At 908, the spectral reflectance is compared with previously stored spectral reflectance data stored in the skin reflectance reference datastore 114. This comparison may comprise a direct comparison, statistical analysis, and so forth and may be set to deem a match as occurring when within a pre-determined threshold. As described above, spectral reflectance of the object across one or more spectral bands may be used to determine the match.

At 910, based at least in part upon the comparison, at least a portion of the object is determined as being skin. For example, as shown here the skin of the hand has been identified as such, while the shirt cuff is designated as "not skin". The augmented reality environment may then utilize this information to accept input from objects which are covered with skin, such as arm, hand, or facial gestures. By differentiating skin from non-skin objects using spectral data, computationally intensive techniques are avoided, and overall system response time may be improved.

CONCLUSION

Although the subject matter has been described in language specific to structural features, it is to be understood that the subject matter defined in the appended claims is not necessarily limited to the specific features described. Rather, the specific features are disclosed as illustrative forms of implementing the claims.

What is claimed is:

1. A system comprising:
    a processor;
    a projector coupled to the processor and configured to illuminate a scene and at least a portion of an object associated with a user with light having a known spectral signature;
    a camera coupled to the processor and configured to acquire image data of the light as reflected from the object;
    a memory accessible by the processor and configured to store one or more skin reflectance references; and
    a skin recognition module accessible by the processor configured to:
        determine a spectral reflectance of the object from the image data acquired by the camera;
        compare the spectral reflectance of the object with a skin reflectance reference stored in the memory; and
        determine an identity of the user based at least in part upon the spectral reflectance of the object and the skin reflectance reference stored in the memory.

2. The system of claim 1, wherein the projector comprises a digital micromirror device.

3. The system of claim 1, wherein illuminating the scene comprises illuminating the scene with structured light.

4. The system of claim 1, wherein illuminating the scene comprises illuminating the scene with a sequence of sub-frames with each sub-frame having a different spectral signature.

5. The system of claim 4, wherein illuminating the scene comprises illuminating the scene with visible light.

6. The system of claim 1, wherein the skin recognition module is further configured to determine the known spectral signature by reflectance from a reference object with known spectral reflectance.

7. The system of claim 1, wherein the skin recognition module is further configured to compensate the spectral reflectance for ambient illumination.

8. One or more non-transitory computer-readable media storing computer-executable instructions that, when executed, cause one or more processors to perform acts comprising:
- illuminating skin of a user with light having a known spectral signature;
- acquiring spectral reflectance data resulting from the illumination;
- comparing the spectral reflectance data with previously stored spectral reflectance;
- determining an adjustment to the previously stored spectral reflectance based at least partly on the spectral reflectance data;
- associating the adjustment with an identity of the user; and
- determining the identity of the user based at least in part on the adjustment.

9. The one or more non-transitory computer-readable storage media of claim 8, wherein the light comprises ultraviolet light.

10. The one or more non-transitory computer-readable storage media of claim 8, wherein illuminating the skin of the user comprises modulating a light source to sequentially generate a plurality of known spectral signatures in differing spectral bands.

11. The one or more non-transitory computer-readable storage media of claim 8, the acts further comprising storing the spectral reflectance data in a skin reflectance reference datastore in association with the user.

12. One or more non-transitory computer-readable media storing computer-executable instructions that, when executed, cause one or more processors to perform acts comprising:
- illuminating at least a portion of a scene containing an object associated with a user with light of a known spectral signature;
- acquiring spectral reflectance data from light reflected by the object in the scene;
- comparing the spectral reflectance data with reflectance reference data; and
- based at least in part upon the spectral reflectance data and the reflectance reference data, estimating an age of the user.

13. The one or more non-transitory computer-readable storage media of claim 12, wherein the acts further comprise determining that the reflectance reference data previously represented skin.

14. The one or more non-transitory computer-readable storage media of claim 12, wherein illuminating the at least the portion of the scene comprises directing a digital micromirror device to project the light with the known spectral signature, and wherein acquiring the spectral reflectance data comprises selectively imaging the scene in wavelengths corresponding to the known spectral signature.

15. The one or more non-transitory computer-readable storage media of claim 12, the acts further comprising acquiring spectral data from light emitted by the object where a spectral band of the light emitted by the object differs from a spectral band of the light illuminating the object.

16. The one or more non-transitory computer-readable storage media of claim 13, wherein the reflectance reference data is stored in a skin reflectance reference datastore that comprises a plurality of pre-determined spectral reflectance data associated with mammalian skin.

17. The one or more non-transitory computer-readable storage media of claim 12, wherein the reflectance reference data is stored in a skin reflectance reference datastore that comprises a plurality of pre-determined spectral reflectance data associated with skin.

18. The one or more non-transitory computer-readable storage media of claim 12, wherein illuminating the at least the portion of the scene comprises directing a digital micromirror device to generate an image with the light of the known spectral signature.

19. The one or more non-transitory computer-readable storage media of claim 12, wherein illuminating the at least the portion of the scene comprises illuminating the scene at a plurality of intervals, each of the plurality of intervals being illuminated with light of different spectral signatures.

20. The one or more non-transitory computer-readable storage media of claim 12, the acts further comprising:
- acquiring an image of at least a portion of the scene with ambient illumination; and
- compensating for the ambient illumination in the spectral reflectance data.

* * * * *